United States Patent [19]

Renvall et al.

[11] 4,045,453
[45] Aug. 30, 1977

[54] METHOD FOR PRODUCING 5-NITRO-2-FURFURYL ACETATE

[75] Inventors: Ilkka Renvall, Suomenoja; Tapio Mattila, Kivenlahti, both of Finland

[73] Assignee: Kemira Oy, Finland

[21] Appl. No.: 605,339

[22] Filed: Aug. 18, 1975

[30] Foreign Application Priority Data
Sept. 6, 1974 Finland .............................. 2624/74

[51] Int. Cl.$^2$ .......................................... C07D 307/70
[52] U.S. Cl. ................................................ 260/347.4
[58] Field of Search ..................................... 260/347.4

[56] References Cited
U.S. PATENT DOCUMENTS
2,490,006  11/1949  Kimel et al. ...................... 260/347.4

Primary Examiner—Henry R. Jiles
Assistant Examiner—Bernard Dentz
Attorney, Agent, or Firm—Bucknam and Archer

[57] ABSTRACT

Furfuryl acetate is reacted at 0°–20° C with a mixture containing strong nitric acid and less than 7 mole, preferably less than 5 mole, acetic anhydride per 1 mole furfuryl acetate, in order to produce an intermediate of nitration, whereafter water is added and the aqueous solution is neutralized to a pH of 4.7–6.5 and finally the mixture is heated to 40°–60° C.

5 Claims, No Drawings

METHOD FOR PRODUCING 5-NITRO-2-FURFURYL ACETATE

BACKGROUND OF THE INVENTION

The invention relates to a method for producing 5-nitro-2-furfuryl acetate from furfuryl acetate and a mixture of strong nitric acid and acetic anhydride. The 5-nitro-2-furfuryl acetate produced by the method according to the invention can as such be used as a biologically active agent against, for example, molds, fungi or bacteria, or as an intermediate in the production of such agents.

The manufacture of 5-nitro-2-furfuryl acetate by nitrating either furfuryl acetate or furfuryl alcohol is previously known [H. Gilman, C.F. Wright, J. Amer. Chem. Soc. 53 (1931), pp. 1923-4]. A mixture of acetic anhydride and fuming nitric acid is used as the nitrating agent. The intermediate formed in the reaction is decomposed by means of pyridine. The use of furfuryl alcohol instead of furfuryl acetate would seem advantageous since one unnecessary production stage, i.e., the esterification of furfuryl alcohol, would be thereby eliminated. However, the method cannot be used on a large scale since 5-nitro-2-furfuryl nitrate, which is an unstable compound, is produced as a by-product. It may explode when it is, for example, hydrolyzed. The formation of this nitrate is mentioned even in the above article. The nitration of furan derivates by H. Gilman's method has been found inconvenient and even dangerous owing to the use of fuming nitric acid. Thus, a general method has later been introduced for the nitration of furan and its derivates (U.S. Pat. No. 2,490,006). It is noted therein that acetic anhydride must be present in a quantity of at least 4 mole, preferably 7.6 mole, and approx. 70-percent nitric acid in a quantity of 1-4 mole, preferably somewhat over 1 mole, per one mole furan derivate. According to the example, the nitration can be performed at 25°-50° C, preferably 40°±3° C. The decomposition of the intermediate can be performed by adding some base and by heating the mixture, the pH of which is 1.79-4.66, preferably 3.7, at 25°-60° C, preferably 55° C, after the addition, until the conversion is complete. The main object is to protect the manufacture of 5-nitro-2-furfural diacetate used as a pharmaceutical raw material, in which case the substance to be nitrated is furfural or its diacetate. For this reason the conditions described in the patent do not correspond, in terms of economy and production techniques, to the optimal ones for nitrating furfuryl acetate. It should also be noted that the yield percentages cited in the patent do not give a correct picture since in several cases they represent only crude yields.

The nitration of furan derivates has also been treated in scientific literature. Thus, H. Saikachi et al. [J. Pharm. Soc. Japan 73 (1953), pp. 1132-6] in their investigations of the nitration of furfuryl acetate obtained a yield of 46% without a catalyst and in the best case 78% when using orthophosphoric acid as a catalyst. It should be noted that the melting point of the final product was only 38°-44° C, which corresponds to a concentration of approx. 90%, and thus it can be estimated that the best yield was approx. 70%. It should also be noted that nitric acid with a concentration of over 70% (d = 1.44 g/ml) and a reaction temperature of −25° C were used for the nitration. T. Sasaki [Bull. Inst. Chem. Research, Kyoto Univ. 33 (1955), pp. 39-48] obtained 60% as his best yield in nitrating furfuryl acetate, when using a reaction temperature of −25° C and sulfuric acid as the catalyst. The said methods are not economical owing to the low reaction temperature. It should be noted that the use of nitric acid with a concentration of over 70% necessitates the said low reaction temperature, and the reactions cannot be performed safely at normal temperatures, e.g., 0°-20° C.

P. Krkoska et al. [Chem. Listy 62 (1968), pp. 182-196] have presented a consistent study on the nitration of furan derivates. According to their study, the nitration of, for example, furfuryl acetate, occurs as follows:

$$(CH_3CO)_2O + HNO_3 \rightleftarrows CH_3COONO_2 + CH_3COOH$$

acetic anhydride — nitric acid — acetyl nitrate

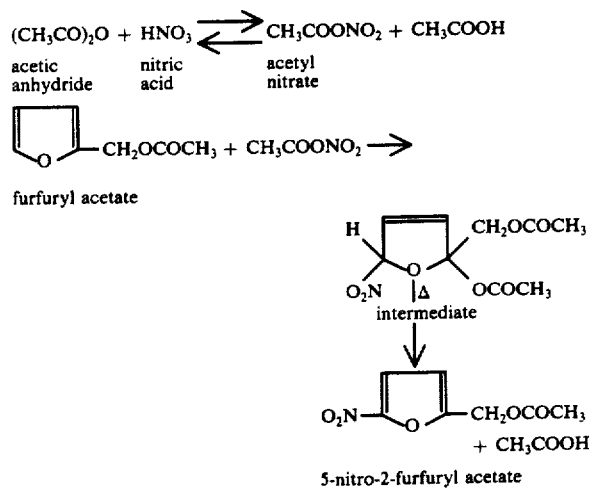

According to the above factors, the yield is substantially dependent on the furan derivate in question. Thus, it can be said that in the nitration of furfural or its diacetate the yields are qualitatively better than in the nitration of furfuryl acetate.

Nevertheless, the reactions are not this simple. On the one hand it is not known what the nitrating agent actually is and it has been claimed that the catalyzing effect of acids is based on the formation of protonized acetyl nitrate [F.G. Bordwell, E. W. Garbisch Jr., J. Amer. Chem. Soc. 82 (1960), pp. 3588-3598]. On the other hand, it is noted in the article by the Czechoslovakians that it has been possible to isolate 3 different intermediates in nitrating furfural.

In our studies we observed deviating from previous practice that furfuryl acetate can be nitrated economically and with a good yield without catalysts; the use of catalysts also increases the waste water load (e.g., phosphoric acid) and complicates the control of the process by promoting oxidation reactions. By the method developed by us, yields of over 75% can be obtained, calculated as pure product.

SUMMARY OF THE INVENTION

According to the invention there is used a temperature of 0-20° C, preferably approx. 10° C, in the nitration since no advantages are gained by using a higher temperature (above 20° C). On the contrary, the system will become unstable and a great quantity of nitrous fumes is produced. It is also advantageous to use less than 5 mole acetic anhydride per one mole furfuryl acetate in the production. When larger acetic anhydride quantities are used, the yield thereby increases but the production costs also increase and the production capacity decreases. The quantity of nitric acid (60-70%) can be varied from 1 to 2 mole.

We have also observed that deviating from previous knowledge, the decomposition conditions of the intermediate of nitration (see above formula) have a crucial effect on the final yield. It is advantageous to perform the decomposition within the pH range 4.7–6.5, preferably 4.7 5.5, at a temperature of 40°–60° C, preferably approx. 50° C, the decomposition period depending on the selected pair of the pH and temperature values. We have noted that a change in the ph from 4.5 to 4.7 definitely causes an increase of approx. 10% in the yield and a raised in the pH to 5.5 an increase of approx. 15%. If the pH is raised to 6.5, the product crystallizes poorly and is impure. The decomposition period depends on the pH at a certain temperature so that, when a higher pH is used, the requisite decomposition period is shorter, the optimum period at approx. 50° C, for example, varying from 25 to 65 minutes. During the decomposition the conversion reaches, depending on the pH, a certain maximum value within a certain period, whereafter the conversion is decreased. In practice the control of the pH is easy with a precision of at least 0.1 units owing to the fact that the highest buffer capacity of acetic acid, present in the mixture in large quantities, is close to pH 4.8, generally within ±1 unit from the said value.

The invention is described below with reference to examples.

EXAMPLE 1

248.4 g (2.43 mole) acetic anhydride was cooled to approx. 2° C and 64.2 g 64.85-percent nitric acid (0.661 mole) was added to it in the course of 55 min so that the temperature remained below 15° C. The mixture was stirred for an additional 20 min and thereafter 71.0 g (0.507 mole) furfuryl acetate (FAc) was added in the course of 70 min so that the temperature remained below 15° C. The mole proportion FAc: $HNO_3$:$Ac_2O$ was thus 1:1.30:4.80. Thereafter 270 ml water was added to the mixture and it was neutralized with a 40-percent NaOH solution to pH 4.4. The mixture was heated in 17min to 52° C and maintained at that for 64 min. The mixture was cooled and kept at a temperature below 10° C for 1 h. The mixture was filtered, washed with water, and dried. 45.1 g product (melting point 41°–43° C) with a concentration of 94.2% was obtained, i.e., the yield was 45.3%.

EXAMPLE 2

The procedure was as in Example 1, but the pH was raised to 4.50 in the neutralization. The mixture was heated in 21 min to 50° C and kept at that for 50 min. 49.2 g product (melting point 41°–43° C) with a concentration of 94.5% was obtained, i.e., the yield was 49.6%.

EXAMPLE 3

The procedure was as in Example 1, but the pH was raised to 4.70 in the neutralization. The mixture was heated in 22 min to 49° C and was kept at that for 40 min. 58.5 g product (melting point 42°–43.5° C) with a concentration of 97.2% was obtained, i.e., the yield was 60.6%.

EXAMPLE 4

The procedure was as in Example 1, but the pH was raised to 4.80 in the neutralization. The mixture was heated in 19 min to 52° C and kept at that for 35 min. 59.7 g product (melting point 42.5°–43.5° C) with a concentration of 97.6% was obtained, i.e., the yield was 62.1%.

EXAMPLE 5

The procedure was as in Example 1, but the pH was raised to 5.5 and the mixture was heated in 19 min to 50° C and was kept at that for 25 min. 64.3 g product (melting point 41°–43° C) with a concentration of 95.1% was obtained, i.e., the yield was 65.2%.

EXAMPLE 6

The procedure was as in Example 3, but the mixture was heated at 40° C for 1 h 15 min. 57.3 g product (melting point 41°–43° C) with a concentration of 95.0% was obtained, i.e., the yield was 58.0%.

EXAMPLE 7

The procedure was as in Example 3, but the heating was performed at 60° C in 19 min. 58.0 g product (melting point 41.5°–43° C) with a concentration of 96.1% was obtained, i.e., the yield was 59.4%.

EXAMPLE 8

The procedure was as in Example 7, except that the addition of furfuryl acetate was performed in the course of 2h at 0°–5° C. 57.5 g product (melting point 41°–43° C) with a concentration of 95.0% was obtained, i.e., the yield was 58.2%.

EXAMPLE 9

The procedure was first as in Example 1 but thereafter 50.4 g (0.360 mole) furfuryl acetate was added in the course of 51 min at a temperature below 13° C. The mixture was stirred for an additional 20 min. Thereafter the procedure continued in the normal manner and the pH was raised to 4.80. The mixture was heated in 23 min to 50° C and was kept at that for 35 min. 51.5 g product (melting point 42.5°–43.5° C) with a concentration of 97.4% was obtained, i.e., the yield was 75.3%. The mole proportion in the experiment was FAc:$HNO_3$: $Ac_2O$ = 1:1.8:6.8.

EXAMPLE 10

A trial series was performed, the conditions being as in Example 1, except that the temperature after the addition of furfuryl acetate was 20° C and that the neutralization pH was changed. The effect of time on the yields at 50° C was studied by taking samples from the mixture and by analyzing them. The following values were obtained: pH 4.4, optimum period 60 min, yield 55.4%; pH 4.8, 35 min, 69.4%; pH 5.5, 25 min, 73.3%; pH 6.5, 20 min, 75.5%. In the latter case the product crystallized poorly after the cooling.

What is claimed is:

1. An improved method for the production of 5-nitro-2-furfuryl acetate, wherein furfuryl acetate is caused to react with a mixture containing concentrated nitric acid and less than 7 mole of acetic anhydride per 1 mole furfuryl acetate, in order to produce an intermediate of nitration, whereafter water is added and the aqueous solution is neutralized, then the mixture is heated to 40°–60° C in order to decompose the intermediate of nitration, the improvement comprising: reacting furfuryl acetate with the mixture consisting of nitric acid having a concentration of 60–70% in the proportion of 1-2 mole per mole of furfuryl acetate and acetic anhydride at 0°–20° C and neutralizing the aqueous solution to a pH of 4.7–6.5 .

2. The improved method of claim 1, wherein the mixture is heated for 15–120 min.

3. The method according to claim 1 wherein the temperature is about 10° C in the reaction of furfuryl acetate with the mixture of nitric acid and acetic anhydride.

4. The method according to claim 1 wherein the aqueous solution is neutralized to a pH of 4.7 – 5.5.

5. The method according to claim 1 wheren furfuryl acetate reacts with a mixture containing nitric acid and less than 5 moles of acetic anhydride per one mole of furfuryl acetate.

* * * * *